(12) United States Patent
Barrick

(10) Patent No.: US 8,768,437 B2
(45) Date of Patent: Jul. 1, 2014

(54) FLUOROSCOPIC IMAGE GUIDED SURGERY SYSTEM WITH INTRAOPERATIVE REGISTRATION

(75) Inventor: Earl F Barrick, McLean, VA (US)

(73) Assignee: Sofamor Danek Holdings, Inc., Memphis, TN (US)

( * ) Notice: Subject to any disclaimer, the term of this patent is extended or adjusted under 35 U.S.C. 154(b) by 1268 days.

(21) Appl. No.: 11/586,105

(22) Filed: Oct. 25, 2006

(65) Prior Publication Data

US 2007/0038079 A1    Feb. 15, 2007

Related U.S. Application Data

(63) Continuation of application No. 10/230,958, filed on Aug. 29, 2002, now Pat. No. 7,130,676, which is a continuation of application No. 09/376,712, filed on Aug. 16, 1999, now Pat. No. 6,477,400.

(60) Provisional application No. 60/097,742, filed on Aug. 24, 1998, provisional application No. 60/097,183, filed on Aug. 20, 1998.

(51) Int. Cl.
*A61B 5/05* (2006.01)

(52) U.S. Cl.
USPC ........... 600/426; 600/407; 600/427; 600/429; 606/65; 606/130; 378/205; 378/206; 378/207

(58) Field of Classification Search
USPC ............ 600/407, 429; 606/130; 378/205–207
See application file for complete search history.

(56) References Cited

U.S. PATENT DOCUMENTS

| | | |
|---|---|---|
| 1,576,781 A | 3/1926 | Phillips |
| 1,735,726 A | 11/1929 | Bornhardt |
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,294,083 A | 12/1966 | Alderson |
| 3,367,326 A | 2/1968 | Frazier |
| 3,439,256 A | 4/1969 | Kahne |

(Continued)

FOREIGN PATENT DOCUMENTS

| | | |
|---|---|---|
| CA | 964149 A1 | 3/1975 |
| DE | 3042343 A1 | 6/1982 |

(Continued)

OTHER PUBLICATIONS

"Prestige Cervical Disc System Surgical Technique", 12 pgs.

(Continued)

*Primary Examiner* — Unsu Jung
*Assistant Examiner* — Joseph M Santos Rodriguez
(74) *Attorney, Agent, or Firm* — Harness, Dickey

(57) ABSTRACT

A system and apparatus allows the tracking of a selected body portion, instrument, or both. A tracking device can be interconnected to a body portion at a mounting site. A procedure can be performed at a location remote from the mounting site of the tracking device. The tracking device can be interconnected with the body in a low invasive manner.

17 Claims, 3 Drawing Sheets

(56) References Cited

U.S. PATENT DOCUMENTS

| | | |
|---|---|---|
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,403,321 A | 9/1983 | Kruger |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,485,815 A | 12/1984 | Amplatz et al. |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,688,037 A | 8/1987 | Krieg |
| 4,701,049 A | 10/1987 | Beckman et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,078,140 A | 1/1992 | Kwoh |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |

(56) References Cited

U.S. PATENT DOCUMENTS

| | | |
|---|---|---|
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,154,717 A | 10/1992 | Matsen, III et al. |
| 5,160,337 A | 11/1992 | Cosman |
| 5,161,536 A | 11/1992 | Vilkomerson et al. |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Muller et al. |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,383,454 A | 1/1995 | Bucholz |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,408,409 A | 4/1995 | Glassman et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,490,196 A | 2/1996 | Rudich et al. |
| 5,494,034 A | 2/1996 | Schlondorff et al. |
| 5,503,416 A | 4/1996 | Aoki et al. |
| 5,513,637 A | 5/1996 | Twiss et al. |
| 5,514,146 A | 5/1996 | Lam et al. |
| 5,515,160 A | 5/1996 | Schulz et al. |
| 5,517,990 A | 5/1996 | Kalfas et al. |
| 5,531,227 A | 7/1996 | Schneider |
| 5,531,520 A | 7/1996 | Grimson et al. |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-haim |
| 5,572,999 A | 11/1996 | Funda et al. |

(56) References Cited

U.S. PATENT DOCUMENTS

| | | | |
|---|---|---|---|
| 5,573,533 A | 11/1996 | Strul | |
| 5,575,794 A | 11/1996 | Walus et al. | |
| 5,575,798 A | 11/1996 | Koutrouvelis | |
| 5,583,909 A | 12/1996 | Hanover | |
| 5,588,430 A | 12/1996 | Bova et al. | |
| 5,590,215 A | 12/1996 | Allen | |
| 5,592,939 A | 1/1997 | Martinelli | |
| 5,595,193 A | 1/1997 | Walus et al. | |
| 5,596,228 A | 1/1997 | Anderton et al. | |
| 5,600,330 A | 2/1997 | Blood | |
| 5,603,318 A | 2/1997 | Heilbrun et al. | |
| 5,611,025 A | 3/1997 | Lorensen et al. | |
| 5,617,462 A | 4/1997 | Spratt | |
| 5,617,857 A | 4/1997 | Chader et al. | |
| 5,619,261 A | 4/1997 | Anderton | |
| 5,622,169 A | 4/1997 | Golden et al. | |
| 5,622,170 A | 4/1997 | Schulz | |
| 5,627,873 A | 5/1997 | Hanover et al. | |
| 5,628,315 A | 5/1997 | Vilsmeier et al. | |
| 5,630,431 A | 5/1997 | Taylor | |
| 5,636,644 A | 6/1997 | Hart et al. | |
| 5,638,819 A | 6/1997 | Manwaring et al. | |
| 5,640,170 A | 6/1997 | Anderson | |
| 5,642,395 A | 6/1997 | Anderton et al. | |
| 5,643,268 A | 7/1997 | Vilsmeier et al. | |
| 5,645,065 A | 7/1997 | Shapiro et al. | |
| 5,646,524 A | 7/1997 | Gilboa | |
| 5,647,361 A | 7/1997 | Damadian | |
| 5,662,111 A | 9/1997 | Cosman | |
| 5,664,001 A | 9/1997 | Tachibana et al. | |
| 5,674,295 A | 10/1997 | Ray et al. | |
| 5,674,296 A | 10/1997 | Bryan et al. | |
| 5,676,673 A | 10/1997 | Ferre et al. | |
| 5,681,260 A | 10/1997 | Ueda et al. | |
| 5,682,886 A | 11/1997 | Delp et al. | |
| 5,682,890 A | 11/1997 | Kormos et al. | |
| 5,690,108 A | 11/1997 | Chakeres | |
| 5,694,945 A | 12/1997 | Ben-Haim | |
| 5,695,500 A | 12/1997 | Taylor et al. | |
| 5,695,501 A | 12/1997 | Carol et al. | |
| 5,697,377 A | 12/1997 | Wittkampf | |
| 5,702,406 A | 12/1997 | Vilsmeier et al. | |
| 5,711,299 A | 1/1998 | Manwaring et al. | |
| 5,713,946 A | 2/1998 | Ben-Haim | |
| 5,715,822 A | 2/1998 | Watkins et al. | |
| 5,715,836 A | 2/1998 | Kliegis et al. | |
| 5,718,241 A | 2/1998 | Ben-Haim et al. | |
| 5,722,594 A | 3/1998 | Farr et al. | |
| 5,727,552 A | 3/1998 | Ryan | |
| 5,727,553 A | 3/1998 | Saad | |
| 5,729,129 A | 3/1998 | Acker | |
| 5,730,129 A | 3/1998 | Darrow et al. | |
| 5,730,130 A | 3/1998 | Fitzpatrick et al. | |
| 5,732,703 A | 3/1998 | Kalfas et al. | |
| 5,735,278 A | 4/1998 | Hoult et al. | |
| 5,738,096 A | 4/1998 | Ben-Haim | |
| 5,740,802 A | 4/1998 | Nafis et al. | |
| 5,741,214 A | 4/1998 | Ouchi et al. | |
| 5,742,394 A | 4/1998 | Hansen | |
| 5,744,953 A | 4/1998 | Hansen | |
| 5,748,767 A | 5/1998 | Raab | |
| 5,749,362 A | 5/1998 | Funda et al. | |
| 5,749,835 A | 5/1998 | Glantz | |
| 5,752,513 A | 5/1998 | Acker et al. | |
| 5,755,725 A | 5/1998 | Druais | |
| RE35,816 E | 6/1998 | Schulz | |
| 5,758,667 A | 6/1998 | Slettenmark | |
| 5,762,064 A | 6/1998 | Polvani | |
| 5,767,669 A | 6/1998 | Hansen et al. | |
| 5,767,699 A | 6/1998 | Bosnyak et al. | |
| 5,767,960 A | 6/1998 | Orman | |
| 5,769,789 A | 6/1998 | Wang et al. | |
| 5,769,843 A | 6/1998 | Abela et al. | |
| 5,769,861 A | 6/1998 | Vilsmeier | |
| 5,772,594 A | 6/1998 | Barrick | |
| 5,775,322 A | 7/1998 | Silverstein et al. | |
| 5,776,064 A | 7/1998 | Kalfas et al. | |
| 5,782,765 A | 7/1998 | Jonkman | |
| 5,787,886 A | 8/1998 | Kelly et al. | |
| 5,792,055 A | 8/1998 | McKinnon | |
| 5,795,294 A | 8/1998 | Luber et al. | |
| 5,797,849 A | 8/1998 | Vesely et al. | |
| 5,799,055 A | 8/1998 | Peshkin et al. | |
| 5,799,099 A | 8/1998 | Wang et al. | |
| 5,800,352 A | 9/1998 | Ferre et al. | |
| 5,800,535 A | 9/1998 | Howard, III | |
| 5,802,719 A | 9/1998 | O'Farrell, Jr. et al. | |
| 5,803,089 A | 9/1998 | Ferre et al. | |
| 5,807,252 A | 9/1998 | Hassfeld et al. | |
| 5,810,008 A | 9/1998 | Dekel et al. | |
| 5,810,728 A | 9/1998 | Kuhn | |
| 5,810,735 A | 9/1998 | Halperin et al. | |
| 5,820,553 A | 10/1998 | Hughes | |
| 5,823,192 A | 10/1998 | Kalend et al. | |
| 5,823,958 A | 10/1998 | Truppe | |
| 5,824,093 A | 10/1998 | Ray et al. | |
| 5,828,725 A | 10/1998 | Levinson | |
| 5,828,770 A | 10/1998 | Leis et al. | |
| 5,829,444 A | 11/1998 | Ferre et al. | |
| 5,831,260 A | 11/1998 | Hansen | |
| 5,833,608 A | 11/1998 | Acker | |
| 5,834,759 A | 11/1998 | Glossop | |
| 5,836,954 A | 11/1998 | Heilbrun et al. | |
| 5,840,024 A | 11/1998 | Taniguchi et al. | |
| 5,840,025 A | 11/1998 | Ben-Haim | |
| 5,843,076 A | 12/1998 | Webster, Jr. et al. | |
| 5,848,967 A | 12/1998 | Cosman | |
| 5,851,183 A | 12/1998 | Bucholz | |
| 5,865,846 A | 2/1999 | Bryan et al. | |
| 5,868,674 A | 2/1999 | Glowinski et al. | |
| 5,868,675 A | 2/1999 | Henrion et al. | |
| 5,871,445 A | 2/1999 | Bucholz | |
| 5,871,455 A | 2/1999 | Ueno | |
| 5,871,487 A | 2/1999 | Warner et al. | |
| 5,873,822 A | 2/1999 | Ferre et al. | |
| 5,880,976 A * | 3/1999 | DiGioia, III et al. | 703/7 |
| 5,882,304 A | 3/1999 | Ehnholm et al. | |
| 5,884,410 A | 3/1999 | Prinz | |
| 5,889,834 A | 3/1999 | Vilsmeier et al. | |
| 5,891,034 A | 4/1999 | Bucholz | |
| 5,891,157 A | 4/1999 | Day et al. | |
| 5,904,691 A | 5/1999 | Barnett et al. | |
| 5,907,395 A | 5/1999 | Schulz et al. | |
| 5,913,820 A | 6/1999 | Bladen et al. | |
| 5,920,395 A | 7/1999 | Schulz | |
| 5,921,992 A | 7/1999 | Costales et al. | |
| 5,923,727 A | 7/1999 | Navab | |
| 5,928,248 A | 7/1999 | Acker | |
| 5,938,603 A | 8/1999 | Ponzi | |
| 5,938,694 A | 8/1999 | Jaraczewski et al. | |
| 5,947,980 A | 9/1999 | Jensen et al. | |
| 5,947,981 A | 9/1999 | Cosman | |
| 5,950,629 A | 9/1999 | Taylor et al. | |
| 5,951,475 A | 9/1999 | Gueziec et al. | |
| 5,951,571 A | 9/1999 | Audette | |
| 5,954,647 A | 9/1999 | Bova et al. | |
| 5,956,796 A | 9/1999 | Lodato | |
| 5,957,844 A | 9/1999 | Dekel et al. | |
| 5,964,796 A | 10/1999 | Imran | |
| 5,967,980 A | 10/1999 | Ferre et al. | |
| 5,967,982 A | 10/1999 | Barnett | |
| 5,968,047 A | 10/1999 | Reed | |
| 5,971,997 A | 10/1999 | Guthrie et al. | |
| 5,976,156 A | 11/1999 | Taylor et al. | |
| 5,980,535 A | 11/1999 | Barnett et al. | |
| 5,983,126 A | 11/1999 | Wittkampf | |
| 5,987,349 A | 11/1999 | Schulz | |
| 5,987,960 A | 11/1999 | Messner et al. | |
| 5,999,837 A | 12/1999 | Messner et al. | |
| 5,999,840 A | 12/1999 | Grimson et al. | |
| 6,001,130 A | 12/1999 | Bryan et al. | |
| 6,006,126 A | 12/1999 | Cosman | |
| 6,006,127 A | 12/1999 | Van Der Brug et al. | |
| 6,013,087 A | 1/2000 | Adams et al. | |

(56) References Cited

U.S. PATENT DOCUMENTS

| | | | |
|---|---|---|---|
| 6,014,580 A | 1/2000 | Blume et al. |
| 6,016,439 A | 1/2000 | Acker |
| 6,019,725 A | 2/2000 | Vesely et al. |
| 6,021,343 A | 2/2000 | Foley et al. |
| 6,024,695 A | 2/2000 | Taylor et al. |
| 6,036,696 A | 3/2000 | Lambrecht et al. |
| 6,050,724 A | 4/2000 | Schmitz et al. |
| 6,059,718 A | 5/2000 | Taniguchi et al. |
| 6,063,022 A | 5/2000 | Ben-Haim |
| 6,071,288 A | 6/2000 | Carol et al. |
| 6,073,043 A | 6/2000 | Schneider |
| 6,076,008 A | 6/2000 | Bucholz |
| 6,096,050 A | 8/2000 | Audette |
| 6,104,944 A | 8/2000 | Martinelli |
| 6,118,845 A | 9/2000 | Simon et al. |
| 6,122,538 A | 9/2000 | Sliwa, Jr. et al. |
| 6,122,541 A | 9/2000 | Cosman et al. |
| 6,127,597 A | 10/2000 | Beyar et al. |
| 6,131,396 A | 10/2000 | Duerr et al. |
| 6,132,465 A | 10/2000 | Ray et al. |
| 6,139,183 A | 10/2000 | Graumann |
| 6,147,480 A | 11/2000 | Osadchy et al. |
| 6,148,117 A | 11/2000 | Lopez et al. |
| 6,149,592 A | 11/2000 | Yanof et al. |
| 6,156,067 A | 12/2000 | Bryan et al. |
| 6,157,853 A | 12/2000 | Blume et al. |
| 6,161,032 A | 12/2000 | Acker |
| 6,165,181 A | 12/2000 | Heilbrun et al. |
| 6,167,145 A | 12/2000 | Foley et al. |
| 6,167,296 A | 12/2000 | Shahidi |
| 6,172,499 B1 | 1/2001 | Ashe |
| 6,175,756 B1 | 1/2001 | Ferre et al. |
| 6,178,345 B1 | 1/2001 | Vilsmeier et al. |
| 6,194,639 B1 | 2/2001 | Botella et al. |
| 6,201,387 B1 | 3/2001 | Govari |
| 6,203,196 B1 | 3/2001 | Meyer et al. |
| 6,203,497 B1 | 3/2001 | Dekel et al. |
| 6,203,543 B1 | 3/2001 | Glossop |
| 6,211,666 B1 | 4/2001 | Acker |
| 6,223,067 B1 | 4/2001 | Vilsmeier et al. |
| 6,226,548 B1 | 5/2001 | Foley et al. |
| 6,233,476 B1 | 5/2001 | Strommer et al. |
| 6,246,231 B1 | 6/2001 | Ashe |
| 6,259,942 B1 | 7/2001 | Westermann et al. |
| 6,273,896 B1 | 8/2001 | Franck et al. |
| 6,285,902 B1 | 9/2001 | Kienzle, III et al. |
| 6,298,262 B1 | 10/2001 | Franck et al. |
| 6,306,177 B1 | 10/2001 | Felt et al. |
| 6,314,310 B1 | 11/2001 | Ben-Haim et al. |
| 6,332,089 B1 | 12/2001 | Acker et al. |
| 6,341,231 B1 | 1/2002 | Ferre et al. |
| 6,351,659 B1 | 2/2002 | Vilsmeier |
| 6,370,224 B1 | 4/2002 | Simon et al. |
| 6,381,485 B1 | 4/2002 | Hunter et al. |
| 6,424,856 B1 | 7/2002 | Vilsmeier et al. |
| 6,427,314 B1 | 8/2002 | Acker |
| 6,428,547 B1 | 8/2002 | Vilsmeier et al. |
| 6,434,415 B1 * | 8/2002 | Foley et al. ............... 600/425 |
| 6,437,567 B1 | 8/2002 | Schenck et al. |
| 6,445,943 B1 | 9/2002 | Ferre et al. |
| 6,470,207 B1 | 10/2002 | Simon et al. |
| 6,474,341 B1 | 11/2002 | Hunter et al. |
| 6,478,802 B2 | 11/2002 | Kienzle, III et al. |
| 6,484,049 B1 | 11/2002 | Seeley et al. |
| 6,490,475 B1 | 12/2002 | Seeley et al. |
| 6,493,573 B1 | 12/2002 | Martinelli et al. |
| 6,498,944 B1 | 12/2002 | Ben-Haim et al. |
| 6,499,488 B1 | 12/2002 | Hunter et al. |
| 6,510,198 B2 | 1/2003 | Simon et al. |
| 6,516,046 B1 | 2/2003 | Frohlich et al. |
| 6,527,443 B1 | 3/2003 | Vilsmeier et al. |
| 6,551,325 B2 | 4/2003 | Neubauer et al. |
| 6,582,467 B1 | 6/2003 | Teitelbaum et al. |
| 6,584,174 B2 | 6/2003 | Schubert et al. |
| 6,602,291 B1 | 8/2003 | Ray et al. |
| 6,609,022 B2 | 8/2003 | Vilsmeier et al. |
| 6,611,700 B1 | 8/2003 | Vilsmeier et al. |
| 6,620,196 B1 | 9/2003 | Trieu |
| 6,640,128 B2 | 10/2003 | Vilsmeier et al. |
| 6,694,162 B2 | 2/2004 | Hartlep |
| 6,701,179 B1 | 3/2004 | Martinelli et al. |
| 6,827,723 B2 | 12/2004 | Carson |
| RE39,133 E | 6/2006 | Clayton et al. |
| 7,130,676 B2 | 10/2006 | Barrick |
| RE40,852 E | 7/2009 | Martinelli et al. |
| RE41,066 E | 12/2009 | Martinelli et al. |
| 2001/0007918 A1 | 7/2001 | Vilsmeier et al. |
| 2002/0095081 A1 | 7/2002 | Vilsmeier et al. |
| 2002/0156363 A1 | 10/2002 | Hunter et al. |
| 2003/0023311 A1 | 1/2003 | Trieu |
| 2003/0072416 A1 | 4/2003 | Rasche et al. |
| 2003/0199984 A1 | 10/2003 | Trieu |
| 2003/0235266 A1 | 12/2003 | Gregerson et al. |
| 2004/0006341 A1 | 1/2004 | Shaolian et al. |
| 2004/0006344 A1 | 1/2004 | Nguyen et al. |
| 2004/0013225 A1 | 1/2004 | Gregerson et al. |
| 2004/0013239 A1 | 1/2004 | Gregerson et al. |
| 2004/0024309 A1 | 2/2004 | Ferre et al. |
| 2004/0039305 A1 | 2/2004 | Eberhart et al. |
| 2004/0039306 A1 | 2/2004 | Eberhart et al. |
| 2004/0152970 A1 | 8/2004 | Hunter et al. |
| 2004/0152972 A1 | 8/2004 | Hunter |
| 2004/0171924 A1 | 9/2004 | Mire et al. |
| 2004/0181149 A1 | 9/2004 | Langlotz et al. |
| 2004/0215071 A1 | 10/2004 | Frank et al. |
| 2005/0085714 A1 | 4/2005 | Foley et al. |
| 2005/0277832 A1 | 12/2005 | Foley et al. |
| 2009/0234217 A1 | 9/2009 | Mire et al. |
| 2009/0290771 A1 | 11/2009 | Frank et al. |
| 2010/0137707 A1 | 6/2010 | Hunter et al. |

FOREIGN PATENT DOCUMENTS

| | | |
|---|---|---|
| DE | 3508730 | 9/1986 |
| DE | 3717871 A1 | 12/1988 |
| DE | 3831278 A1 | 3/1989 |
| DE | 3838011 A1 | 7/1989 |
| DE | 4213426 A1 | 10/1992 |
| DE | 4225112 C1 | 12/1993 |
| DE | 4233978 C1 | 4/1994 |
| DE | 19715202 A1 | 10/1998 |
| DE | 19751761 A1 | 10/1998 |
| DE | 19832296 | 2/1999 |
| DE | 19747427 A1 | 5/1999 |
| DE | 10085137 | 11/2002 |
| EP | 0062941 | 10/1982 |
| EP | 0119660 A1 | 9/1984 |
| EP | 0155857 | 9/1985 |
| EP | 0319844 | 6/1989 |
| EP | 0326768 A2 | 8/1989 |
| EP | 350996 A1 | 1/1990 |
| EP | 0350996 A1 | 1/1990 |
| EP | 0419729 A1 | 4/1991 |
| EP | 0427358 | 5/1991 |
| EP | 0456103 | 11/1991 |
| EP | 0581704 | 2/1994 |
| EP | 0651968 | 5/1995 |
| EP | 0655138 | 5/1995 |
| EP | 0894473 A2 | 2/1999 |
| EP | 0908146 A2 | 4/1999 |
| EP | 0930046 A2 | 7/1999 |
| EP | 964149 A1 | 12/1999 |
| FR | 7904241 | 2/1979 |
| FR | 2417970 | 9/1979 |
| FR | 2618211 | 1/1989 |
| GB | 2094590 A | 9/1982 |
| GB | 2164856 A | 4/1986 |
| JP | 62327 | 1/1983 |
| JP | 63240851 | 10/1988 |
| JP | 2765738 T | 4/1991 |
| JP | 3267054 | 11/1991 |
| JP | 6194639 | 7/1994 |
| WO | WO-8809151 | 12/1988 |
| WO | WO-8905123 | 6/1989 |

(56) References Cited

FOREIGN PATENT DOCUMENTS

| | | |
|---|---|---|
| WO | WO-9005494 A1 | 5/1990 |
| WO | WO-9103982 A1 | 4/1991 |
| WO | WO-9104711 A1 | 4/1991 |
| WO | WO-9107726 | 5/1991 |
| WO | WO-9203090 | 3/1992 |
| WO | WO-9206645 | 4/1992 |
| WO | WO-9404711 A1 | 3/1994 |
| WO | WO-9404938 | 3/1994 |
| WO | WO-9423647 | 10/1994 |
| WO | WO-9424933 A1 | 11/1994 |
| WO | WO-9507055 A1 | 3/1995 |
| WO | WO-9611624 | 4/1996 |
| WO | WO-9632059 A1 | 10/1996 |
| WO | WO-9736192 A1 | 10/1997 |
| WO | WO-9749453 A1 | 12/1997 |
| WO | WO-9808554 A1 | 3/1998 |
| WO | WO-9838908 | 9/1998 |
| WO | WO-9915097 A2 | 4/1999 |
| WO | WO-9921498 A1 | 5/1999 |
| WO | WO-9923956 A1 | 5/1999 |
| WO | WO-9926549 A1 | 6/1999 |
| WO | WO-9927839 A2 | 6/1999 |
| WO | WO-9929253 A1 | 6/1999 |
| WO | WO-9933406 A1 | 7/1999 |
| WO | WO-9937208 A1 | 7/1999 |
| WO | WO-9938449 A1 | 8/1999 |
| WO | WO-9952094 A1 | 10/1999 |
| WO | WO-9960939 A1 | 12/1999 |
| WO | WO-0064367 A1 | 11/2000 |
| WO | WO-0130437 A1 | 5/2001 |
| WO | WO-2004070573 A2 | 8/2004 |

OTHER PUBLICATIONS

Adams et al., "Orientation Aid for Head and Neck Surgeons," Innov. Tech. Biol. Med., vol. 13, No. 4, 1992, pp. 409-424.

Adams et al., Computer-Assisted Surgery, IEEE Computer Graphics & Applications, pp. 43-51, (May 1990).

Barrick, "Distal Locking Screw Insertion Using a Cannulated Drill Bit: Technical Note," Journal of Orthopaedic Trauma, vol. 7, No. 3, 1993, pp. 248-251.

Barrick, E.F., "Journal of Orthopaedic Trauma: Distal Locking Screw Insertion Using a Cannulated Drill Bit: Technical Note," Raven Press, vol. 7, No. 3, 1993, pp. 248-251.

Barrick, et al., "Prophylactic Intramedullary Fixation of the Tibia for Stress Fracture in a Professional Athlete," Journal of Orthopaedic Trauma, vol. 6, No. 2, pp. 241-244 (1992).

Barrick, et al., "Technical Difficulties with the Brooker-Wills Nail in Acute Fractures of the Femur," Journal of Orthopaedic Trauma, vol. 4, No. 2, pp. 144-150 (1990).

Batnitzky, S., Price, H.I., Lee, K.R., Cook, P.N., Cook, L.T., Fritz, S.L., Dwyer, S.J. Watts, C., Three-Dimensional Computer Reconstructions of Brain Lesions from Surface Contours Provided by Computed Tomography: A Prospectus, Neurosurgery, vol. 11, No. 1, Part 1, 1982, pp. 73-84.

Benzel et al., "Magnetic Source Imaging: A Review of the Magnes System of Biomagnetic Technologies Incorporated," Neurosurgery, vol. 33, No. 2 (Aug. 1993), pp. 252-259.

Bergstrom et al. Stereotaxic Computed Tomography, Am. J. Roentgenol, vol. 127 pp. 167-170 (1976).

Bouazza-Marouf, et al., "Robotic-Assisted Internatl Fixation of Fermoral Fractures," IMECHE., pp. 51-58 (1995).

Brack et al., "Accurate X-ray Based Navigation in Computer-Assisted Orthopedic Surgery," CAR '98, pp. 716-722.

Brown, R., M.D., A Stereotactic Head Frame for Use with CT Body Scanners, Investigative Radiology .COPYRGT. J.B. Lippincott Company, pp. 300-304 (Jul.-Aug. 1979).

Bryan, "Bryan Cervical Disc System Single Level Surgical Technique", Spinal Dynamics, 2002, pp. 1-33.

Bucholz et al., "Variables affecting the accuracy of stereotactic localizationusing computerized tomography," Journal of Neurosurgery, vol. 79, Nov. 1993, pp. 667-673.

Bucholz, R.D., et al. Image-guided surgical techniques for infections and trauma of the central nervous system, Neurosurg. Clinics of N.A., vol. 7, No. 2, pp. 187-200 (1996).

Bucholz, R.D., et al., A Comparison of Sonic Digitizers Versus Light Emitting Diode-Based Localization; Interactive Image-Guided Neurosurgery, Chapter 16, pp. 179-200 (1993).

Bucholz, R.D., et al., Intraoperative localization using a three dimensional optical digitizer, SPIE—The Intl. Soc. for Opt. Eng., vol. 1894, pp. 312-322 (Jan. 17-19, 1993).

Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics andComputer-Assisted Surgery, Grenoble, France, pp. 459-466 (Mar. 19-22, 1997).

Champleboux et al., "Accurate Calibration of Cameras and Range Imaging Sensors: the NPBS Method," IEEE International Conference on Robotics and Automation, Nice, France, May 1992.

Champleboux, G., Utilisation de Fonctions Splines pour la Mise au Point D'un Capteur Tridimensionnel sans Contact, Quelques Applications Medicales, Jul. 1991.

Cinquin, P., et al., "Computer Assisted Medical Interventions," IEEE Engineering in Medicine and Biology, May/Jun. 1995, pp. 254-263.

Cinquin, P., Lavallee, S., Demongeot, J., Computer Assisted Medical Interventions, International Advanced Robotics Programme, Sep. 1989, pp. 63-65.

Clarysse, P., Gibon, D., Rousseau, J., Blond, S., Vasseur, C., Marchandise, X., A Computer-Assisted System for 3-D Frameless Localization in Stereotaxic MRI, IEEE Transactions on Medical Imaging, vol. 10, No. 4, Dec. 1991, pp. 523-529.

Colchester, A.C.F., Hawkes, D.J., Information Processing in Medical Imaging, Lecture Notes in Computer Science, 12.sup.th International Conference, IPMI, Jul. 1991, pp. 136-141.

Cutting M.D. et al., Optical Tracking of Bone Fragments During Craniofacial Surgery, Second Annual International Symposium on Medical Robotics and Computer Assisted Surgery, pp. 221-225, (Nov. 1995).

Dams, L., Knepper, A., Krybus, W., Meyer-Ebrecht, D., Pfeifer, G., Ruger, R., Witte, M., Aide au Reperage Tridimensional pour la Chirurgie de la Base du Crane, Innov. Tech. Biol. Med., vol. 13, No. 4, 1992, pp. 409-424.

Feldmar, J., et al., "3D-2D Projective Registration of Free-Form Curves and Surfaces," Rapport de recherche (Inria Sophia Antipolis), 1994, pp. 1-44.

Foley, "The StealthStation: Three-Dimensional Image-Interactive Guidance for the Spine Surgeon," Spinal Frontiers, Apr. 1996, pp. 7-9.

Foley, J.D., Van Dam, A., Fundamentals of Interactive Computer Graphics, The Systems Programming Series, Chapter 7, Jul. 1984, pp. 245-266.

Foley, K.T., Smith, K.R., Bucholz, R.D., Image-guided Intraoperative Spinal Localization, Intraoperative Neuro-protection, Chapter 19, 1996, pp. 325-340.

Friets, E.M., et al, A Frameless Stereotaxic Operating Microscope for Neurosurgery, IEEE Trans. on Biomed. Eng., vol. 36, No. 6, pp. 608-617 (Jul. 1989).

Gallen, C.C., et al., Intracranial Neurosurgery Guided by Functional Imaging, Surg. Neurol., vol. 42, pp. 523-530 (1994).

Galloway, R.L. et al., Interactive Image-Guided Neurosurgery, IEEE Trans. on Biomed. Eng., vol. 89, No. 12, pp. 1226-1231 (1992).

Galloway, R.L., Jr. et al, Optical localization for interactive, image-guided neurosurgery, SPIE, vol. 2164, (May 1, 1994) pp. 137-145.

Germano, "Instrumentation, Technique and Technology", Neurosurgery, vol. 37, No. 2, Aug. 1995, pp. 348-350.

Gildenberg, P.L., Kaufman, H.H., Murthy, K.S. Calculation of Stereotactic Coordinates from the Computed Tomographic Scan, Neurosurgery, vol. 10, No. 5, May 1982, pp. 580-586.

Gomez, C.R., et al., Transcranial Doppler Ultrasound Following Closed Head Injury: Vasospasm or Vasoparalysis?, Surg. Neurol., vol. 35, pp. 30-35 (1991).

Gonzalez, R.C., Digital Image Fundamentals, Digital Image Processing, Second Edition, 1987, pp. 52-54.

(56) References Cited

OTHER PUBLICATIONS

Gottesfeld Brown, L.M., et al., "Registration of Planar Film Radiographs with Computer Tomography," Proceedings of MMBIA, Jun. '96, pp. 42-51.
Grimson, W.E.L., An Automatic Registration Method for Frameless Stereotaxy, Image Guided Surgery, and enhanced Reality Visualization, IEEE, pp. 430-436 (1994).
Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6, pp. 62-69 (Jun. 1999).
Gueziec, A.P., et al., "Registration of Computer Tomography Data to a Surgical Robot Using Fluoroscopy: A Feasiblity Study," Computer Science/Mathematics, Sep. 27, 1996, 6 pages.
Guthrie, B.L., Graphic-Interactive Cranial Surgery: The Operating Arm System, Handbook of Stereotaxy Using the CRW Apparatus, Chapter 13, (1994) pp. 193-211.
Hamadeh et al, "Kinematic Study of Lumbar Spine Using Functional Radiographies and 3D/2D Registration," TIMC UMR 5525—IMAG. (1997).
Hamadeh, A., et al., "Automated 3-Dimensional Computer Tomographic and Fluoroscopic Image Registration," Computer Aided Surgery (1998), 3:11-19.
Hamadeh, A., et al., "Towards Automatic Registration Between CT and X-ray Images: Cooperation Between 3D/2D Registration and 2D Edge Detection," MRCAS '95, pp. 39-46.
Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).
Hatch, et al., "Reference-Display System for the Integration of CT Scanning and the Operating Microscope", Proceedings of the Eleventh Annual Northeast Bioengineering Conference, May 1985, pp. 252-254.
Hatch, J.F., Reference-Display System for the Integration of CT Scanning and the Operating Microscope, Thesis, Thayer School of Engineering, Oct. 1984, pp. 1-189.
Heilbrun et al., "Preliminary experience with Brown-Roberts-Wells (BRW) computerized tomography stereotaxic guidance system," Journal of Neurosurgery, vol. 59, Aug. 1983, pp. 217-222.
Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).
Heilbrun, M.P., Computed Tomography—Guided Stereotactic Systems, Clinical Neurosurgery, Chapter 31, pp. 564-581 (1983).
Heilbrun, M.P., et al., Stereotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94-98 (1992).
Henderson, J.M., Smith, K.R., Bucholz, R.D., An Accurate and Ergonomic Method of Registration for Image-Guided Neurosurgery, Computerized Medical Imaging and Graphics, vol. 18, No. 4, Jul.-Aug. 1994, pp. 273-277.
Hoerenz, P., The Operating Microscope I., Optical Principles, Illumination Systems, and Support Systems, Journal of Microsurgery, vol. 1, 1980, pp. 364-369.
Hofstetter, R., et al., "Fluoroscopy Based Surgical Navigation-Concept and Clinical Applications," Computer Assisted Radiology and Surgery, 1997, pp. 956-960.
Horner et al., "A Comparison of CT-Stereotaxic Brain Biopsy Techniques," Investigative Radiology, Sep.-Oct. 1984, pp. 367-373.
Hounsfield, G.N., Computerized transverse axial scanning (tomography): Part I. Description of system, British Journal of Radiology, vol. 46, No. 552, Dec. 1973, pp. 1016-1022.
Jacques, S., Sheldon, C.H., McCann, G.D., A Computerized Microstereotactic Method to Approach, 3-Dimensionally Reconstruct, Remove and Adjuvantly Treat Small CNS Lesions, Applied Neurophysiology, vol. 43, 1980, pp. 176-182.
Jacques, S., Sheldon, C.H., McCann, G.D., Freshwater, D.B., Rand, R., Computerized three-dimensional stereotaxic removal of small central nervous system lesion in patients, J. Neurosurg., vol. 53, Dec. 1980, pp. 816-820.
Joskowicz, L., et al., "Computer-Aided Image-Guided Bone Fracture Surgery: Concept and Implementation," CAR '98, pp. 710-715.
Kall, B., The Impact of Computer and Imgaging Technology on Stereotactic Surgery, Proceedings of the Meeting of the American Society for Stereotactic and Functional Neurosurgery, pp. 10-22 (1987).
Kato, A., et al., A frameless, armless navigational system for computer-assisted neurosurgery, J. Neurosurg., vol. 74, pp. 845-849 (May 1991).
Kelly et al., "Computer-assisted stereotaxic laser resection of intraaxial brain neoplasms," Journal of Neurosurgery, vol. 64, Mar. 1986, pp. 427-439.
Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).
Kelly, P.J., Computer-Directed Stereotactic Resection of Brain Tumors, Neurologica Operative Atlas, vol. 1, No. 4, pp. 299-313 (1991).
Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).
Kelly, P.J., Kall, B., Goerss, S., Alker, G.J., Jr., Precision Resection of Intra-Axial CNS Lesions by CT-Based Stereotactic Craniotomy and Computer Monitored CO2 Laser, Acta Neurochirurgica, vol. 68, 1983, pp. 1-9.
Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).
Kim, W.S. et al., A Helmet Mounted Display for Telerobotics, IEEE, pp. 543-547 (1988).
Klimek, L., et al., Long-Term Experience with Different Types of Localization Systems in Skull-Base Surgery, Ear, Nose & Throat Surgery, Chapter 51, (1996) pp. 635-638.
Kosugi, Y., et al., An Articulated Neurosurgical Navigation System Using MRI and CT Images, IEEE Trans. on Biomed, Eng. vol. 35, No. 2, pp. 147-152 (Feb. 1988).
Krybus, W., et al., Navigation Support for Surgery by Means of Optical Position Detection, Computer Assisted Radiology Proceed. of the Intl. Symp. CAR'91 Computed Assisted Radiology, pp. 362-366 (Jul. 3-6, 1991).
Kwoh, Y.S., Ph.D., et al., A New Computerized Tomographic-Aided Robotic Stereotaxis System, Robotics Age, vol. 7, No. 6, pp. 17-22 (Jun. 1985).
Laitinen et al., "An Adapter for Computed Tomography-Guided, Stereotaxis," Surg. Neurol., 1985, pp. 559-566.
Laitinen, "Noninvasive multipurpose stereoadapter," Neurological Research, Jun. 1987, pp. 137-141.
Lavalle, S., et al., "Image guided operating robot: a clinical application in steroetactic neurosurgery," Proceedings of the 1992 IEEE International Conference on Robotics and Automation, May 1992, pp. 618-624.
Lavallee et al., "Computer Assisted Spine Surgery: A Technique for Accurate Transpedicular Screw Fixation Using CT Data and a 3-D Optical Localizer," TIMC, Faculte de Medecine de Grenoble. (1995).
Lavallee, S., A New System for Computer Assisted Neurosurgery, IEEE Engineering in Medicine & Biology Society 11.sup.th Annual International Conference, 1989, pp. 0926-0927.
Lavallee, S., Brunie, L., Mazier, B., Cinquin, P., Matching of Medical Images for Computed and Robot Assisted Surgery, IEEE EMBS, Orlando, 1991.
Lavallee, S., Cinquin, P., Demongeot, J., Benabid, A.L., Marque, I., Djaid, M., Computer Assisted Driving of a Needle into the Brain, Proceedings of the International Symposium: CAR 89, pp. 416-420.
Lavallee, S., Cinquin, P., Demongeot, J., Benabid, A.L., Marque, I., Djaid, M., Computer Assisted Interventionist Imaging: The Instance of Stereotactic Brain Surgery, North Holland MEDINFO 89, Part 1, 1989, pp. 613-617.

(56) References Cited

OTHER PUBLICATIONS

Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).
Lavallee, S., et al., Computer Assisted Medical Interventions, NATO ASI Series, vol. F 60, 3d Imaging in Medic., pp. 301-312 (1990).
Lavallee, S., Szeliski, R., Brunie, L., Matching 3-D Smooth Surfaces with Their 2-D Projections using 3-D Distance Maps, SPIE, vol. 1570, Geometric Methods in Computer Vision, 1991, pp. 322-336.
Leavitt, D.D., et al., Dynamic Field Shaping to Optimize Stereotactic Radiosurgery, I.J. Rad. Onc. Biol. Physc., vol. 21, pp. 1247-1255 (1991).
Leksell, L., Jernberg, B., Steretaxis and Tomography—A Technical Note, ACTA Neurochirurgica, vol. 52, 1980, pp. 1-7.
Lemieux, L., et al., "A Patient-to-Computer-Tomography Image Registration Method Based on Digitally Reconstructed Radiographs," Med. Phys. 21 (11), Nov. 1994, pp. 1749-1760.
Levin, D.N., Hu, X., Tan, K.K., Galhotra, S., Pelizzari, C.A., Chen, G.T.Y., Beck, R.N., Chen, C., Cooper, M.D., Mullan, J.F., Hekmatpanah, J., Spire, J., The Brain: Integrated three-dimensional Display of MR and PET Images, Radiology, vol. 172, No. 3, Sep. 1989, pp. 783-789.
Maurer, Jr., et al., Registration of Head CT Images to Physical Space Using a Weighted Combination of Points and Surfaces, IEEE Trans. on Med. Imaging, vol. 17, No. 5, pp. 753-761 (Oct. 1998).
Mazier, B., Lavallee, S., Cinquin, P., Chirurgie de la Colonne Vertebrale Assistee par Ordinateur: Application au Vissage Pediculaire, Innov. Tech. Biol. Med., vol. 11, No. 5, 1990, pp. 559-566.
Mazier, B., Lavallee, S., Cinquin, P., Computer Assisted Interventionist Imaging: Application to the Vertebral Column Surgery, Annual International Conference of the IEEE Engineering in Medicine and Biology Society, vol. 12, No. 1, 1990, pp. 0430-0431.
McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).
Merloz, et al., "Computer Assisted Spine Surgery", Clinical Assisted Spine Surgery, No. 337, (1997) pp. 86-96.
Ng, W.S. et al., Robotic Surgery—A First-Hand Experience in Transurethral Resection of the Prostate Surgery, IEEE Eng. in Med. and Biology, pp. 120-125 (Mar. 1993).
Pelizzari et al., "Interactive 3D Patient-Image Registration," Information Processing in Medical Imaging, 12th International Conference, IPM '91, Jul. 7-12, 136-141 (A.C.F. Colchester et al. eds. 1991).
Pelizzari, C.A., Chen, G.T.Y., Halpern, H., Chen, C.T., Cooper, M.D., No. 528—Three Dimensional Correlation of PET, CT and MRI Images, The Journal of Nuclear Medicine, vol. 28, No. 4, Apr. 1987, p. 682.
Pelizzari, C.A., Chen, G.T.Y., Spelbring, D.R., Weichselbaum, R.R., Chen, C., Accurate Three-Dimensional Registration of CT, PET, and/or MR Images of the Brain, Journal of Computer Assisted Tomography, Jan./Feb. 1989, pp. 20-26.
Penn, R.D., et al., Stereotactic Surgery with Image Processing of Computerized Tomographic Scans, Neurosurgery, vol. 3, No. 2, pp. 157-163 (Sep.-Oct. 1978).
Philips, R., et al., "Images Guided Orthopaedic Surgery Design and Analysis," Trans Inst MC, vol. 17, No. 5, 1995, pp. 251-264.
Potamianos, P., et al., "Intra-Operative Imaging Guidance for Keyhole Surgery Methodology and Calibration," First International Symposium on Medical Robotics and Computer Assisted Surgery, Sep. 22-24, 1994, pp. 98-104.
Reinhardt, H., et al., A Computer-Assisted Device for Intraoperative CT-Correlated Localization of Brain Tumors, pp. 51-58 (1988).
Reinhardt, H.F. et al., Sonic Stereometry in Microsurgical Procedures for Deep-Seated Brain Tumors and Vascular Malformations, Neurosurgery, vol. 32, No. 1, pp. 51-57 (Jan. 1993).
Reinhardt, H.F., et al., Mikrochirugische Entfernung tiefliegender Gefa.beta.mi .beta.bildungen mit Hilfe der Sonar-Stereometrie (Microsurgical Removal of Deep-Seated Vascular Malformations Using Sonar Stereometry). Ultraschall in Med. 12, pp. 80-83(1991).
Reinhardt, H.F., Landolt, H., CT-Guided "Real Time" Stereotaxy, ACTA Neurochirurgica, 1989.
Reinhardt, Hans. F., Neuronavigation: A Ten-Year Review, Neurosurgery, (1996) pp. 329-341.
Roberts, D.W., Strohbehn, J.W., Hatch, J.F., Murray, W., Kettenberger, H., A frameless stereotaxic integration of computerized tomographic imaging and the operating microscope, J. Neurosurg., vol. 65, Oct. 1986, pp. 545-549.
Rosenbaum, A.E., Lunsford, L.D., Perry, J.H., Computerized Tomography Guided Stereotaxis: A New Approach, Applied Neurophysiology, vol. 43, No. 3-5, 1980, pp. 172-173.
Sautot, Pascal Phillippe, "Vissage Pediculaire Assiste Par Ordinateur," Sep. 20, 1994.
Schueler et al., "Correction of Image Intensifier Distortion for Three-Dimensional X-Ray Angiography," SPIE Medical Imaging 1995, vol. 2432, pp. 272-279.
Selvik, G., et al., "A Roentgen Stereophotogrammetric System," Acta Radiologica Diagnosis, 1983, pp. 343-352.
Shelden, C.H., McCann, G., Jacques, S., Lutes, H.R., Frazier, R.E., Katz, R., Kuki, R., Development of a computerized microstereotaxic method for localization and removal of minute CNS lesions under direct 3-D vision, J. Neuro-surg., vol. 52, 1980,pp. 21-27.
Simon, D.A., Accuracy Validation in Image-Guided Orthopaedic Surgery, Second Annual Intl. Symp. on Med. Rob. an Comp-Assisted surgery, MRCAS (1995), pp. 185-192 (undated).
Smith et al., "The Neurostation.TM.—A Highly Accurate, Minimally Invasive Solution to Frameless Stereotactic Neurosurgery," Computerized Medical Imaging and Graphics, vol. 18, Jul.-Aug. 1994, pp. 247-256.
Smith, K.R., Bucholz, R.D., Computer Methods for Improved Diagnostic Image Display Applied to Stereotactic Neurosurgery, Automedical, vol. 14, 1992, pp. 371-382.
Smith, K.R., et al. Multimodality Image Analysis and Display Methods for Improved Tumor Localization in Stereotactic Neurosurgery, Annul Intl. Conf. of the IEEE Eng. in Med. and Biol. Soc., vol. 13, No. 1, p. 210 (1991).
Tan, K., Ph.D., et al., A frameless stereotactic approach to neurosurgical planning based on retrospective patient-image registration, J Neurosurgy, vol. 79, pp. 296-303 (Aug. 1993).
Thompson, et al., A System for Anatomical and Functional Mapping of the Human Thalamus, Computers and Biomedical Research, vol. 10, pp. 9-24 (1977).
Trobraugh, J.W., et al., Frameless Stereotactic Ultrasonography: Method and Applications, Computerized Medical Imaging and Graphics, vol. 18, No. 4, pp. 235-246 (1994).
Viant, W.J., et al., "A Computer Assisted Orthopaedic System for Distal Locking of Intramedullary Nails," Proc. of MediMEC '95, Bristol, 1995, pp. 86-91.
Von Hanwhr et al., Foreword, Computerized Medical Imaging and Graphics, vol. 18, No. 4, pp. 225-228, (Jul.-Aug. 1994).
Wang, M.Y., et al., An Automatic Technique for Finding and Localizing Externally Attached Markers in CT and MR Volume Images of the Head, IEEE Trans. on Biomed. Eng., vol. 43, No. 6, pp. 627-637 (Jun. 1996).
Watanabe, E., M.D., et al., Open Surgery Assisted by the Neuronavigator, a Stereotactic, Articulated, Sensitive Arm, Neurosurgery, vol. 28, No. 6, pp. 792-800 (1991).
Watanabe, E., Watanabe, T., Manaka, S.,Mayanagi, Y., Takakura, K., Three-Dimensional Digitizer (Neuronavigator): New Equipment for Computed Tomography-Guided Stereotaxic Surgery, Surgical Neurology, vol. 27, No. 6, Jun. 1987, pp. 543-547.
Watanabe, H., Neuronavigator, Igaku-no-Ayumi, vol. 137, No. 6, May 10, 1986, pp. 1-4.
Weese et al., "An Approach to 2D/3D Registration of a Vertebra in 2D X-ray Fluoroscopies with 3D CT Images," (1997) pp. 119-128.

\* cited by examiner

FLUOROSCOPIC IMAGE GUIDED SURGERY SYSTEM WITH INTRAOPERATIVE REGISTRATION

CROSS-REFERENCE TO RELATED APPLICATIONS

This application is a continuation of U.S. patent application Ser. No. 10/230,958, filed on Aug. 29, 2002, now U.S. Pat. No. 7,130,676 issued on Oct. 31, 2006; which is a continuation of U.S. patent application Ser. No. 09/376,712, filed on Aug. 16, 1999, now U.S. Pat. No. 6,477,400; which claims the benefit of both U.S. Provisional Application Ser. No. 60/097,742, filed on Aug. 24, 1998 and U.S. Provisional Application Ser. No. 60/097,183, filed on Aug. 20, 1998. The disclosures of which are hereby incorporated by reference.

BACKGROUND OF THE INVENTION

In orthopaedic surgery it is often necessary to insert a guide pin for a cannulated screw, drill bit, or other screw (hereafter referred to as a fixation device) into a bone at a predetermined trajectory. Pre-operative planning depends on two-dimensional radiographic images which typically consist of two views taken at approximately right angles to one another. From these two views it is possible to determine the shape and structure of a long bone. Using that method, the path of insertion for a guide pin for a cannulated screw, drill bit, or screw is accurately determined. However, in practice the actual aiming of a fixation device is an inaccurate art, as the object bone is often seen only at one surface or is not seen at all and, therefore, positioning is dependent on fluoroscopic visualization. This method is also time consuming as the C-arm images must be taken separately and the drapes must be rearranged each time an image is taken. As boney tissue is unyielding, the track of the pin or drill bit is determined by the angular approach before entering the object bone. This angular approach is difficult to determine under normal circumstances and often multiple attempts are needed, as feedback is obtained from repeated fluoroscopic images. Existing methods of calculating the proper angle of guide pin for a cannulated hip screw insertion for hip pinning involve placing data manually into a computer program, which in turn outputs an angle of guide pin for a cannulated hip screw insertion.

Radiation exposure is a necessary part of any procedure for calculating the proper angle of a guide pin, drill bit, or screw insertion. Radiation exposure is considered to be a hazard. Ionizing radiation has no safe threshold of exposure below which it ceases to have adverse effects, although an arbitrary level is assumed. There has been a recent upward revision of risk estimates of radiation exposure, but absolute levels of safe exposure remain unknown. Exposure to the surgical team as well as the patient during orthopaedic procedures using fluoroscopy is a universal concern. Consequently, a reduction in the amount of radiation exposure is highly desirable.

Operative stereotactic localization using either frames or three-dimensional digitizers is currently being used in neurosurgery or otolaryngology. Those methods require the use of computed axial tomography (CT) or magnetic resonance imaging (MRI) prior to surgery. They also involve placing markers on the scalp prior to the imaging study of the head. The markers must be left in the same position until surgery is performed in order to confirm intraoperative registration. Such imaging studies are routinely performed for most intracranial procedures but are impractical for most orthopaedic procedures, especially those involving long bones. A probe marked with light emitting diodes (LEDs) or other digitizing emitters is used to localize these markers or pins using a three-dimensional digitizing device at the time of surgery. A disadvantage of this system is that the images are normally obtained hours before use; thus, the images used are not up to date (real time) and are often not reflective of the current condition of the object bone.

Registration markers cannot be used on the outside of the body in most orthopaedic cases as the skin does not adhere to the underlying bone. Pre-operative registration for robotic placement of the femoral components for total hip arthroplasty requires the use of a separate procedure to insert screws for such markers. Such a separate procedure is highly impractical for routine orthopaedic procedures.

An alternative method of registration for image guided surgery requires wide operative exposure, such as in pedicle screw insertion in spine surgery. The various fiducials are determined by touching prominent or distinctive anatomic points with a digitizing probe as employed by the stereotactic localization system. Furthermore, the system also requires preoperative computed axial tomography.

A system using fluoroscopic images to guide the insertion of a fixation device employs tracking with a three-dimensional optical digitizer. This optical digitizer is used to determine the position in six degrees of freedom of a portable fluoroscopy machine ("C-arm fluoroscope") and the object region of the skeleton. Light emitting diodes ("LEDs") are placed in distinctive patterns on the C-arm. Another set of LEDs are attached to the bone with a percutaneous screw device, such as a reference bar. A computer program records these positions in relation to an optical position sensor.

X-rays are then taken with the C-arm fluoroscope with the two positions of the tube at approximate right angles to one another. The optical position sensor can thus determine where the C-arm is positioned in relation to LED markers attached to the reference bar attached to the object section of the skeleton. The exact position is determined by using two-dimensional image registration, matching the outline of the bone in two planes. In this system, three or more distinctly shaped radiographic markers are attached to threaded tipped registration pins inserted percutaneously. Thus, the object portion of the skeleton is localized in six degrees of freedom by the optical digitizer.

The computer program relates the position of the object bone with or without fiducial markers in the two fields to determine the exact relative position of the object bone seen on the two images. Once those two images are displayed on monitors, no further x-rays are needed. Thus, a substantial reduction in the amount of ionizing radiation results. The images displayed are those familiar to the surgeon but with the usual distortion eliminated.

A drill with attached LEDs inserts the fixation device in the position in the bone that the surgeon chooses based on the supplied information. The three-dimensional optical digitizer determines the position of the drill in relation to the optical digitizer camera and the object section of the skeleton with its fiducials. A graphic display of the fixation device of predetermined length is then overlaid on the images of the object bone in near real time. Thus, the position of the inserted pin or drill bit can be adjusted immediately.

SUMMARY OF THE INVENTION

The present invention allows an orthopaedic surgeon to safely determine the precise trajectory of insertion of a fixation device into an object bone and to check the accuracy of the procedure using real time feedback.

The present invention remedies the disadvantages of the prior art system of using fluoroscopic images and an optical digitizer to localize the object bone and the track of the intended fixation device.

The same three-dimensional optical digitizer is used to determine the position in six degrees of freedom of a portable fluoroscopy machine (C-arm fluoroscope) and the object regional of the skeleton. Light emitting diodes (LEDs) are placed in distinctive patterns on the C-arm and attached to the bone, the latter with a percutaneous screw device, such as a reference bar. A computer program records these positions in relation to an optical position sensor.

X-rays are then taken with the C-arm fluoroscope with the two positions of the tube at approximate right angles to one another. The optical position sensor can thus determine where the C-arm is positioned in relation to LED markers attached to the reference bar attached to the object section of the skeleton. The exact position is determined by using two-dimensional image registration, matching the outline of the bone in two planes.

The difference from prior art is that, in this invention, distinctly shaped radiographic markers are not required to match the position of the object bone with the image thereof. Matching, or registration, is performed by a single registration pin or other object that is seen on both x-ray views. The spherical shape of the femoral head may be used to increase the accuracy of the registration if the invention is used for hip surgery. When used for inserting distal locking screws for intramedullary nails, the presence of the nail alone with the holes for the interlocking screws can be used as fiducial reference marker. This method of image registration is clearly superior to the use of three special registration pins with specialized markers.

The fixation device can then be inserted using a drill or drill guide that has attached LEDs that serve as means to localize it in six degrees of freedom. The graphic representation of the guide pin for a cannulated screw, drill bit, or extended projection of the drill guide positioned appropriately on the pair of monitors can be used to determine the correct trajectory.

Accurate localization of a hip screw in the femoral head has been shown in an important clinical study to result in much superior results than if the screw is placed eccentrically. Accurate aiming of an interlocking screw in an intramedullary nail is difficult to obtain using all current techniques. It is improved by this invention such that operative time and radiation are markedly reduced.

This invention has the advantage of simplifying the operation and making it more acceptable to use computer assisted surgery to improve accuracy.

DETAILED DESCRIPTION OF THE PREFERRED EMBODIMENTS

Figure 1:
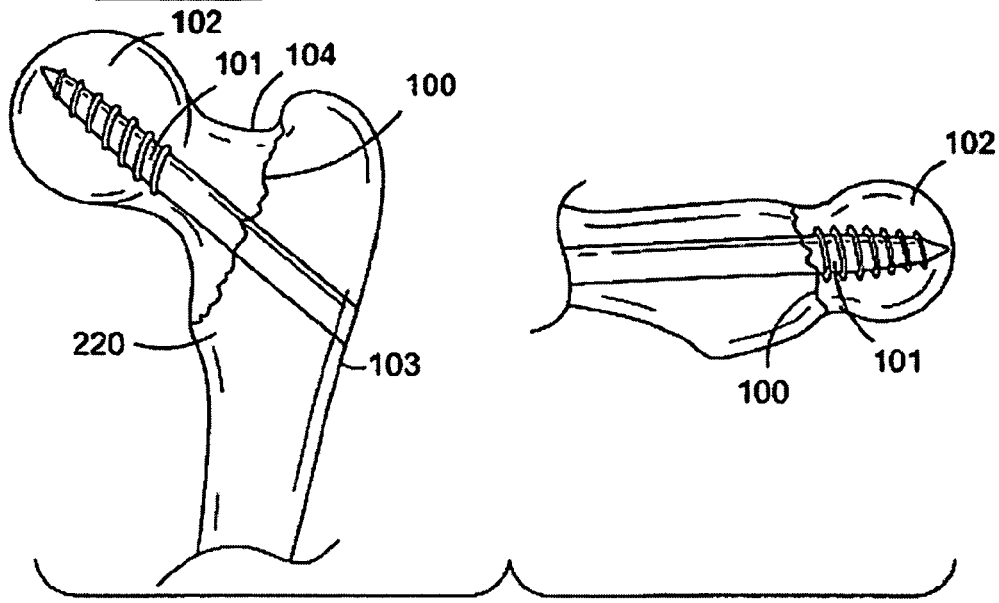
FIG. 1 is an illustration of anterior and lateral x-ray views of the proximal femur with an intertrochanteric fracture with a hip screw in optimal position.
Figure 2A:
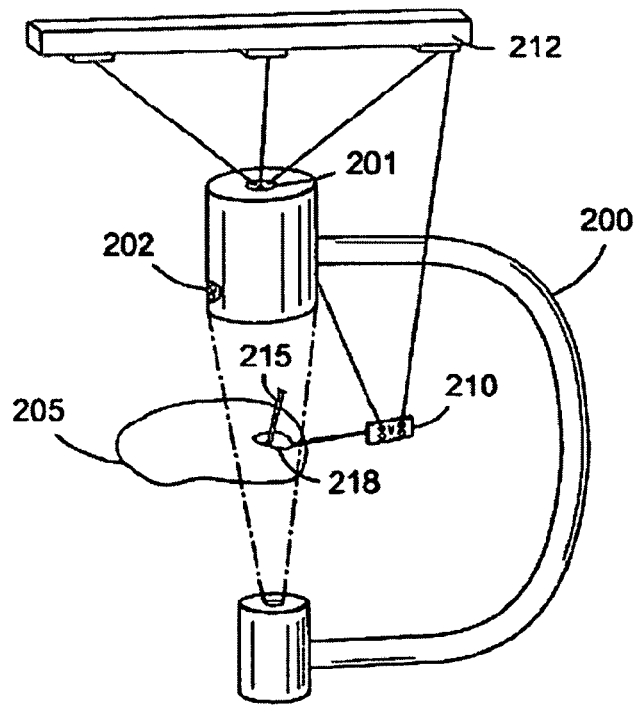
FIGS. 2A & 2B are perspective illustrations of the intraoperative setting showing the C-arm fluoroscope, an optical digitizer camera, and the object body.
Figure 2B:
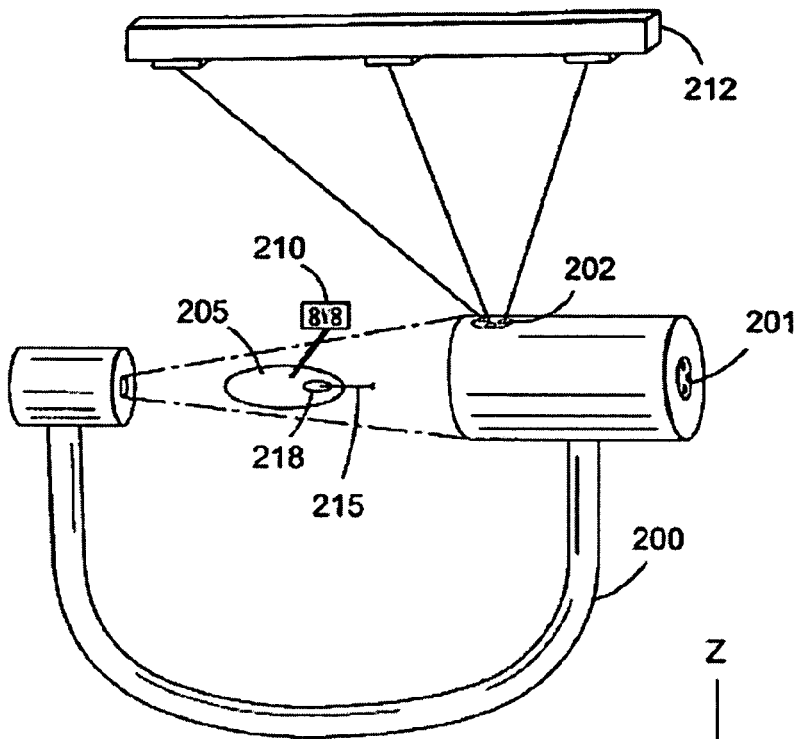
Figure 4:
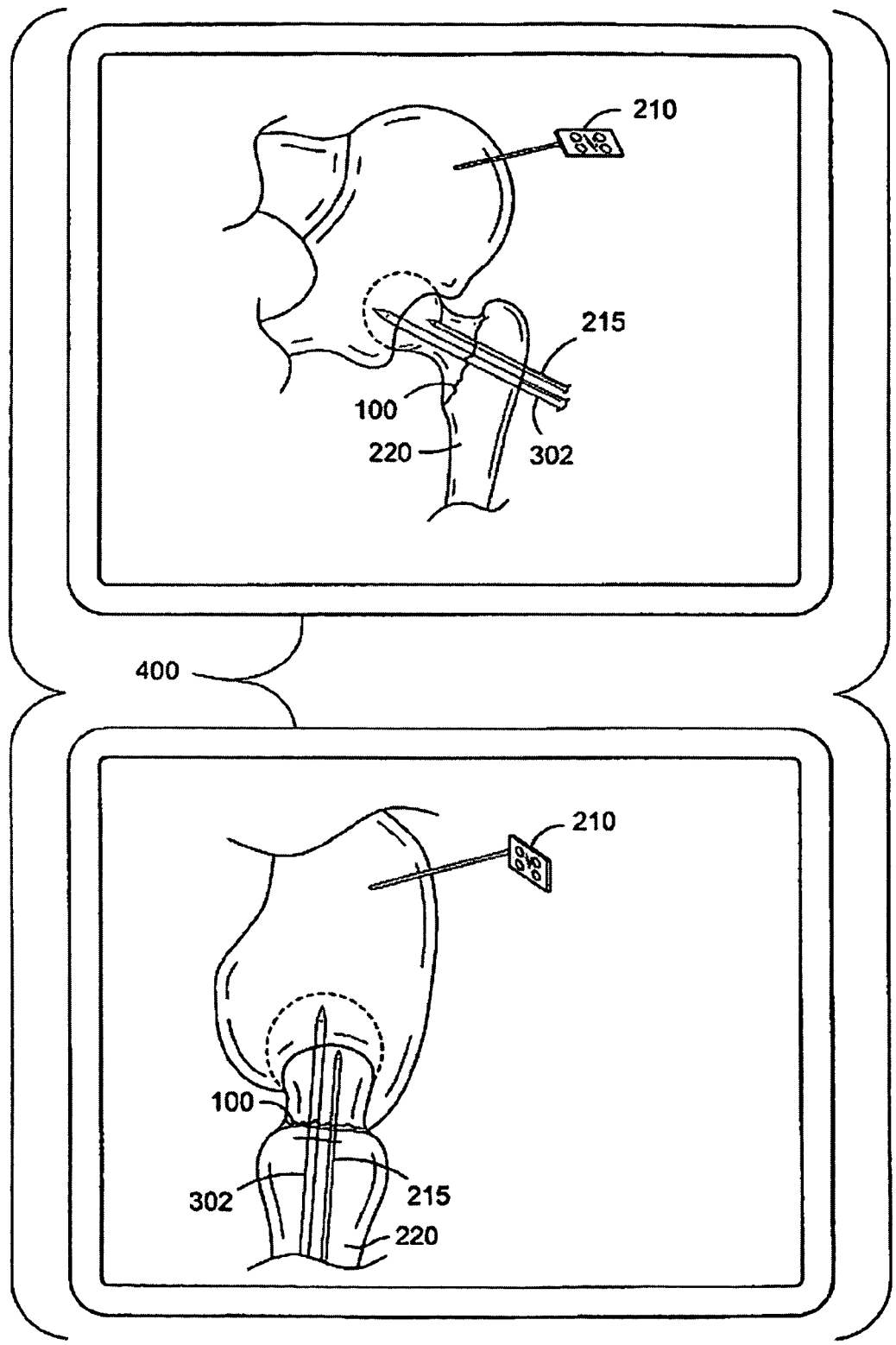
FIG. 4 is an illustration of a pair of computer monitor screens with radiographic images of the object bone at positions approximately 90 degrees to one another, with a single registration pin and a reference bar in place, and with the graphic image of a guide pin 302 for a cannulated hip screw superimposed.

The operation for the internal fixation of intertrochanteric hip fracture 100 requires a guide pin for a cannulated hip screw, and subsequently cannulated screw 101, to be placed into femoral head 102 from lateral cortex 103 of proximal femur 220 via femoral neck 104, as illustrated in FIG. 1. Guide pin 302 for cannulated hip screw 101 determines the position of cannulated screw 101. The ideal position of the guide pin for a cannulated hip screw, and thus screw 101, is entirely within bone. The end of the pin, and screw 101, is best positioned very near the subcortical bone but should not penetrate the cortex and thus enter the hip joint. The best results of an intertrochanteric fracture 100 must have been shown to occur when large screw 101 used is in the center of the femoral head at the subcortical bone. This position is normally obtained by placing the guide pin for a cannulated hip screw by estimation and by following its course on entry with repeated x-rays views in two planes. C-arm fluoroscope 200, as seen in FIG. 2, must be moved from one position of the other. Repeated attempts may be needed before the optimal position of guide pin 302, as seen in FIG. 4, for a cannulated hip screw can be obtained. Operating time and radiation exposure would be reduced by using image guided surgery. The accuracy and thus long term results would be improved.

In this system of fluoroscopic image guided orthopaedic surgery with intraoperative registration, light emitting diodes (LEDs) are attached to portable C-arm fluoroscopy 200 at two sites. One LED 201 is placed to determine the position of C-arm 200 when in the upright position as in FIG. 2A, which corresponds to the anteroposterior x-ray view when the patient 205 is supine. Another LED 202 is located so that it is seen by optical digitizer camera 212 when C-arm 200 is horizontal as in FIG. 2B, corresponding to the lateral x-ray view.

Patient 205 is lying supine in traction on a fracture table during the procedure. After appropriate sterile preparation, reference bar 210 with LEDs is inserted through a small incision into ilium 218. The optical digitizer software is programmed to recognize the region of the skeleton attached to reference bar 210 as a rigid body. The rigid body computer model thus remains immobile, and the other objects with LEDs attached move in relation to this rigid body. Femur 220 must remain immobile in relation to ilium 218, which is usually the case. FIG. 4 illustrates x-ray views seen with the fluoroscope.

Then proximal femur 220 is exposed through a routine lateral incision. Registration pin 215 is then inserted in proximal femur 220. X-rays at approximate right angles are then taken in the standard anteroposterior and lateral views. When C-arm 200 is in the upright position (FIG. 2A), LEDs 201 facing optical digitizer camera 212 indicate to the computer where C-arm 200 is in three dimensional space. Thus the computer can calculate the plane in which body 205 lies—in relation to reference bar 210. When C-arm 200 is in the horizontal position (FIG. 2B), LEDs 202 are now facing optical digitizer camera 212 and indicate again where C-arm 200 is in three dimensional space when in this position. The computer can then calculate exactly where body 205 and femur 220 seen on x-ray are in relation to optical digitizer camera 212. This calculation is possible with registration pin 215 and femur 220 now being recorded in two positions. The method of finding the position of registration pin 215 is a type of image registration.

Figure 3:
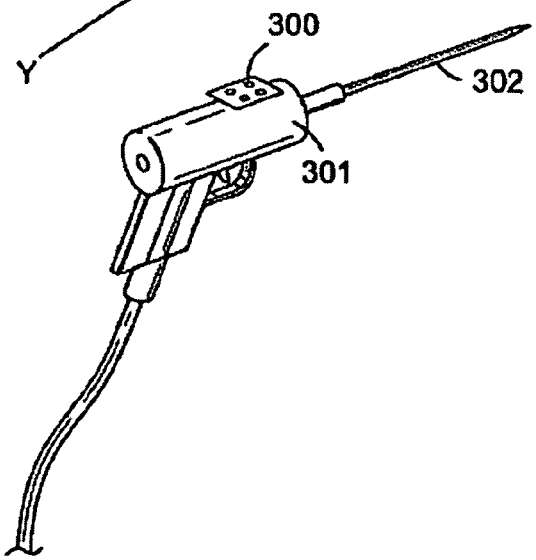
FIG. 3 is an illustration of a drill with mounted light emitting diodes.

LEDs 300 are mounted on the body of drill 301 as shown in FIG. 3. Guide pin 302 for cannulated hip screw 101 is placed in position into drill 301.

The signals emitted from LEDs 300 on drill 301 are received by optical digitizer camera 212 when placed in the operating field. The computer can then determine the position of drill 301 to reference bar 210 and thus to femur 220. A graphic image of guide pin 302 for a cannulated hip screw can then be displayed on each monitor 400 as seen in FIG. 4 to show the relationship of guide pin 302 for a cannulated hip screw to femur 220 in both the anteroposterior and the lateral views. Guide pin 302 for cannulated hip screw 101 can then be inserted in the desired position with image guidance.

If reference bar 210 should be moved or loosened, registration can be done again during the operation just be repeating the two x-ray views. Once registration pin 215 is in place, identification of fiducials by the tedious method of touching points with a probe is unnecessary. The accuracy of image registration with registration pin 215 or other object is much greater than with previous methods.

What is claimed is:

1. A method of performing an image guided surgery on an anatomy, comprising:
    obtaining image data of a region of the anatomy including a bone portion and a pelvis of the anatomy, wherein obtaining image data includes obtaining a first fluoroscopic two-dimensional x-ray image and a second fluoroscopic two-dimensional x-ray image that is at an angle to the first fluoroscopic x-ray image;
    attaching a reference bar to the pelvis, wherein the pelvis defines a first portion of a joint;
    selecting a bone portion separate and different from the pelvis in the anatomy and defining a second portion of the joint, wherein the reference bar is not inserted into the bone portion;
    placing only a single registration pin in the selected bone portion;
    registering the obtained image data to the selected bone portion with the single registration pin and the outline of the bone portion in the first fluoroscopic two-dimensional x-ray image and the second fluoroscopic two-dimensional x-ray image;
    tracking the reference bar to determine a location of the pelvis;
    tracking and guiding an instrument with a tracking device to determine a location of the instrument relative to the reference bar attached to the pelvis; and
    while tracking and guiding the instrument, performing a procedure with the instrument on the bone portion that is separate and different from the pelvis to which the reference bar is attached, wherein the procedure includes fusing a first segment of the bone portion and a second segment of the bone portion wherein at least one of the first segment or the second segment form the joint with the pelvis;
    calculating a plane in which the pelvis lies in relation to the reference bar;
    wherein registering the obtained image data to the selected bone portion further includes using a spherical femoral head to increase registration accuracy.

2. The method of claim 1, further comprising:
    maintaining the bone portion immobile relative to the pelvis while performing the procedure.

3. The method of claim 2, further comprising:
    displaying the determined location of the instrument superimposed on the registered obtained image data to show the location of the instrument relative to a location of the bone portion based upon the tracked position of the instrument and the reference bar.

4. The method of claim 3, wherein tracking the instrument includes tracking a drill driving a bone screw.

5. The method of claim 1, further comprising:
    sterilizing an appropriate portion of the anatomy including:
        selecting a portion of the anatomy for attachment of the reference bar;
        sterilizing the selected portion of the anatomy for attaching the reference bar; and
        inserting the reference bar through a small incision to attach the reference bar to the pelvis.

6. The method of claim 1, wherein tracking the reference bar to determine the location of the pelvis and tracking the instrument with the tracking device to determine the location of the instrument includes determining with a system the locations of the reference bar and the instrument in three dimensional space.

7. The method of claim 1, wherein fusing the first segment of the bone portion and the second segment of the bone portion includes internal fixation of an intertrochanteric hip fracture with a screw.

8. The method of claim 7, wherein the first segment and the second segment are both segments of the same bone portion and the hip fracture is a fracture of a femoral neck of the bone portion;
    wherein the joint includes a hip joint.

9. The method of claim 8, further comprising:
    inserting a guide pin into the femur with the instrument while tracking the instrument; and
    driving a cannulated screw over the guide pin once the guide pin is inserted into the femur.

10. The method of claim 9, further comprising:
    determining a location of the guide pin based on the obtained image data prior to inserting the guide pin.

11. The method of claim 9, further comprising:
    tracking a position of an imaging device with a tracking system relative to the reference bar while obtaining the image data.

12. A method of performing an image guided surgery on an anatomy, comprising:
    obtaining image data of a hip joint region of the anatomy including the hip joint defined by a pelvis of the anatomy and a spherical femoral head of a femur of the anatomy, wherein obtaining image data includes obtaining a first fluoroscopic two-dimensional x-ray image and a second fluoroscopic two-dimensional x-ray image that is at an angle to the first fluoroscopic x-ray image;
    attaching a reference bar to an ilium of the pelvis;
    tracking the reference bar to determine a location of the pelvis and the femur;
    registering the obtained image data to the hip joint of the anatomy including the pelvis and the femur using only a single registration pin inserted into the femur and the spherical femoral head to increase registration accuracy; and
    tracking a tracking device attached to an instrument to determine a location of the instrument relative to the femur based on tracking the reference bar attached to the pelvis while performing a procedure with the instrument on the femur in the anatomy, wherein performing the procedure includes fusing a first segment of the femur and a second segment of the femur, wherein at least one of the first segment or the second segment form the hip joint with the pelvis;
    displaying the determined location of the instrument superimposed on the registered obtained image data to show the location of the instrument relative to the location of the femur based upon the tracked position of the tracking device attached to the instrument that is tracked relative to tracked location of the reference bar;

calculating a plane in which the pelvis lies in relation to the reference bar;

wherein the femur is naturally moveable relative to the pelvis, is separate from the pelvis, and is different from the pelvis;

wherein the reference bar remains unfixed to the femur.

13. The method of claim 12, wherein performing a procedure includes:

inserting a guide pin into the femur with the instrument; and displaying a determined location of the guide pin to show the location of the guide pin relative to the location of the femur based upon the tracked position of the tracking device attached to the instrument and the reference bar.

14. The method of claim 13, wherein performing the procedure further includes:

passing a cannulated screw over the inserted guide pin into the femur for internal fixation of an intertrochanteric hip fracture.

15. A method of performing an image guided surgery on an anatomy, comprising:

obtaining a first fluoroscopic two-dimensional x-ray image data of a region of the anatomy including a femoral joint between a pelvis of the anatomy and a spherical femoral head of a femur of the anatomy with an imaging device at a first position;

obtaining a second fluoroscopic two-dimensional x-ray image data of the region of the anatomy including the femoral joint between the pelvis of the anatomy and the spherical femoral head of the femur of the anatomy with the imaging device at a second position that is at an angle to the first position;

attaching a reference bar to an illium of the pelvis;

attaching only a single registration pin to the femur at a location away from the illium;

registering the first fluoroscopic two-dimensional x-ray image data and the second fluoroscopic two-dimensional x-ray image data to at least the spherical femoral head of the femur of the anatomy using the single registration pin and an outline of the femur in the first fluoroscopic two-dimensional x-ray image and the second fluoroscopic two-dimensional x-ray image, wherein registering includes using the spherical femoral head to increase registration accuracy;

calculating a plane in which the pelvis lies in relation to the reference bar;

tracking the reference bar to determine a location of the pelvis and the femur; and tracking an instrument with a tracking device to determine a location of the instrument relative to the reference bar attached to the pelvis while performing a procedure with the instrument on the femur portion in the anatomy, wherein fusing a first segment of the femur and a second segment of the femur, wherein at least one of the first segment or the second segment form the joint with the pelvis;

wherein the femur is naturally moveable relative to the pelvis, is separate from the pelvis, and is different from the pelvis;

wherein the reference bar remains unfixed to the femur.

16. The method of claim 15, further comprising:

driving a guide pin to the spherical femoral head of the femur while tracking the instrument; and driving a cannulated bone screw over the guide pin for fixation of a fracture of a femoral neck of the femur.

17. The method of claim 16, further comprising:

illustrating a location of the guide pin on a monitor based on tracking the instrument to which the guide pin is coupled.

* * * * *